US006312673B2

(12) United States Patent
Richard et al.

(10) Patent No.: US 6,312,673 B2
(45) Date of Patent: Nov. 6, 2001

(54) PHOTOSTABILIZED SUNSCREEN COMPOSITIONS COMPRISING DIBENZOYLMETHANE COMPOUNDS AND BENZYLIDENECAMPHOR-SUBSTITUTED SILANES/ORGANOSILOXANES

(75) Inventors: Hervé Richard, Villepinte; Serge Forestier, Claye Souilly, both of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/761,827

(22) Filed: Jan. 18, 2001

Related U.S. Application Data

(62) Division of application No. 09/350,910, filed on Jul. 12, 1999, now Pat. No. 6,200,552.

(30) Foreign Application Priority Data

Jul. 10, 1998 (FR) .................................................. 98 08937

(51) Int. Cl.⁷ .............................. A61K 7/42; A61K 7/44; A61K 7/00
(52) U.S. Cl. .............................. 424/59; 424/60; 424/400; 424/401

(58) Field of Search ................................. 424/59, 60, 400, 424/401

(56) References Cited

U.S. PATENT DOCUMENTS

| 5,951,968 | 9/1999 | Forestier et al. ........................ 424/59 |
| 6,004,540 | 12/1999 | Richard et al. ........................ 424/59 |

FOREIGN PATENT DOCUMENTS

| 0712855 | 5/1996 | (EP) . |
| 93/10745 | 6/1993 | (WO) . |
| 94/04131 | 3/1994 | (WO) . |

*Primary Examiner*—Shelley A. Dodson
(74) *Attorney, Agent, or Firm*—Burns, Doane, Swecker & Mathis, L.L.P.

(57) ABSTRACT

Improvedly photostable, topically applicable cosmetic/dermatological sunscreen compositions well suited for enhanced photoprotection of human skin and/or hair against the damaging effects of UV-A and UV-B irradiation, particularly solar radiation, comprise (i) a photoprotecting effective amount of at least one dibenzoylmethane UV-screening compound, and (ii) an amount of at least one silane or organosiloxane substituted by a benzylidenecamphor functional group effective to photostabilize said at least one dibenzoylmethane UV-screening compound (i).

31 Claims, No Drawings

PHOTOSTABILIZED SUNSCREEN COMPOSITIONS COMPRISING DIBENZOYLMETHANE COMPOUNDS AND BENZYLIDENECAMPHOR-SUBSTITUTED SILANES/ORGANOSILOXANES

CROSS-REFERENCE TO PRIORITY APPLICATION

This application is a divisional of Application Ser. No. 09/350,910, filed Jul. 12, 1999, now U.S. Pat. No. 6,200,552, incorporated by reference herein in its entirety and relied upon, which claims priority under 35 U.S.C. §119 of FR-98/08937, filed Jul. 10, 1998, assigned to the assignee hereof and hereby expressly incorporated by reference.

BACKGROUND OF THE INVENTION

1. Technical Field of the Invention

The present invention relates to improving the photostability of at least one dibenzoylmethane sunscreen compound with respect to UV radiation, by intimately admixing therewith an effective photostabilizing amount of a silane or organosiloxane compound bearing a benzylidenecamphor substituent.

2. Description of the Prior Art

It is known to this art that light radiation with wavelengths of from 280 nm to 400 nm promotes tanning of the human epidermis, and that irradiation with wavelengths more particularly ranging from 280 to 320 nm, i.e., UV-B irradiation, causes erythema and skin burns which can be harmful to the development of a natural tan. For these reasons, as well as for aesthetic reasons, a constant demand exists for controlling this natural tanning and, also, the coloration of the skin; such UV-B radiation should thus be screened from the skin.

It is also known to this art that UV-A irradiation, with wavelengths of from 320 to 400 nm, which tans the skin, is apt to induce an adverse change therein, in particular in the case of sensitive skin or skin which is continually exposed to solar radiation. UV-A radiation in particular causes a loss of elasticity of the skin and the appearance of wrinkles, promoting premature aging. Such irradiation promotes triggering of the erythemal reaction or enhances this reaction in certain individuals and may even be the source of phototoxic or photoallergic reactions. Thus, for aesthetic and cosmetic reasons such as conserving the skins, natural elasticity, for example, an ever-increasing number of subjects wish to control the effect of UV-A rays on their skin. It is thus desirable to also screen UV-A radiation from the skin.

In this regard, one particularly advantageous class of UV-A screening agents currently includes dibenzoylmethane derivatives, and in particular 4-(tert-butyl)-4'-methoxydibenzoylmethane, which have high intrinsic absorption power. These dibenzoylmethane derivatives, which are compounds that are well known per se as screening agents that are active in the UV-A range, are particularly described in FR-A-2,326,405 and FR-A-2,440,933, as well as in EP-A-0,114,607; 4-(tert-butyl)-4'-methoxydibenzoylmethane is moreover commercially available under the trademark "PARSOL 1789" from Givaudan.

Unfortunately, it has been determined that dibenzoylmethane derivatives are compounds that are relatively sensitive to ultraviolet radiation (especially UV-A radiation), namely, more specifically, they exhibit an annoying tendency to be degraded more or less rapidly under the influence of such radiation. Thus, this substantial lack of photochemical stability of dibenzoylmethane derivatives in the face of the ultraviolet radiation to which they are by nature intended to be subjected, does not guarantee constant protection during prolonged exposure to the sun, such that, in a restricting manner, repeated applications at regular and close time intervals must be carried out by the user in order to obtain effective protection of the skin against UV radiation.

Thus, EP-A-0,709,080 describes combining dibenzoylmethane derivatives with benzalmalonate derivatives in order to reduce the photoinstability of said dibenzoylmethane derivatives. Nonetheless, the photostabilization of dibenzoylmethane derivatives with respect to UV radiation constitutes, to date, a problem which has not yet been solved completely satisfactorily.

FR-2,607,996 and WO-94/04131 describe combining dibenzoylmethane derivatives with hydrocarbon-based benzylidenecamphor derivatives such as 3-(4-methylbenzylidene)camphor in order to reduce the photoinstability of said dibenzoylmethane derivatives.

Another difficulty, independent of the one indicated above, encountered with dibenzoylmethane derivatives is that these are lipophilic sunscreen agents with the particular feature, and also present the disadvantage of being solid at room temperature. Accordingly, formulating same into antisun cosmetic compositions entails certain constraints as regards their processing, in particular for determining solvents for properly dissolving same, whether alone or in combination with other screening agents. In this regard, oils have been typically employed such as esters, and more particularly $C_{12}$–$C_{15}$ alkyl benzoates ("Finsolv TN" marketed by Finetex), or triglycerides, and in particular $C_8$–$C_{12}$ fatty acid triglycerides ("Miglyol 812" marketed by Hüls), but these various products exhibit solubilizing properties with respect to the aforesaid screening agents that remain insufficient.

Sunscreen formulations based on dibenzoylmethane derivatives and on 3-(4-methylbenzylidene)camphor as described in FR-2,607,996 and WO-94/04131 do not obviate this problem of solubility of said dibenzoylmethane derivatives completely satisfactorily.

SUMMARY OF THE INVENTION

It has now unexpectedly and surprisingly been found that formulating the dibenzoylmethane derivatives indicated above with an effective amount of a silane or organosiloxane compound containing a benzylidenecamphor substituent, substantially and markedly improves the photochemical stability (or photostability) of these same dibenzoylmethane derivatives.

It has also been determined that the silane or organosiloxane compounds containing a benzylidenecamphor functional group according to the present invention are effective photostabilizing agents, which is also very surprising compared with the known hydrocarbon-based organic screening agents derived from benzylidenecamphor, and constitute a family of solvents which are particularly noteworthy for the screening agents of dibenzoylmethane derivative type such as, for example, 4-(tert-butyl)-4'-methoxydibenzoylmethane; this permits, for an equal amount of solvent, formulating greater amounts of screening agents.

Thus, the present invention features enhancing the stability of at least one dibenzoylmethane compound with respect to UV radiation, by intimately formulating therewith an effective photostabilizing amount of a silane or organosiloxane derivative bearing a benzylidenecamphor substituent.

The cosmetic and/or dermatological compositions according to this invention present the advantage of being particularly photostable, even after prolonged exposure to UV-A and UV-B radiation. Such radiation can be of natural origin (sunlight) or artificial origin (UV lamp).

The present invention, thus, also features formulating a silane or organosiloxane compound containing a benzylidenecamphor functional group into a cosmetic or dermatological composition including at least one dibenzoylmethane sunscreen compound, to enhance the stability of said dibenzoylmethane sunscreen with respect to UV radiation.

DETAILED DESCRIPTION OF BEST MODE AND SPECIFIC/PREFERRED EMBODIMENTS OF THE INVENTION

More particularly according to the present invention, the subject dibenzoylmethane sunscreens are well known per se and are described, in particular, in FR-A-2,326,405, FR-A-2,440,933 and EP-A-0,114,607.

Consistent herewith, it is intended, of course, to formulate one or more of said dibenzoylmethane compounds into the compositions of the invention.

Among the dibenzoylmethane derivatives suitable for formulation according to the present invention, particularly exemplary are:

2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane,;
2,4-dimethyl-4'-methoxydibenzoylmethane;
2,6-dimethyl-4-tert-butyl-4'-methoxydibenzoylmethane; and
4,4'-dimethoxydibenzoylmethane.

Among the dibenzoylmethane derivatives compounds indicated above, most particularly preferred is 4-(tert-butyl)-4'-methoxydibenzoylmethane, in particular that marketed under the trademark "Parsol 1789" by Givaudan. This sunscreen agent has the following structural formula:

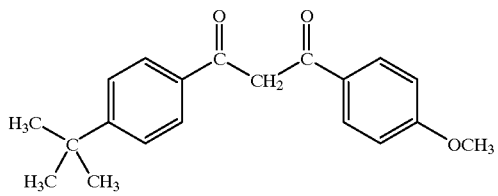

Another dibenzoylmethane derivative which is preferred according to the present invention is 4-isopropyldibenzoylmethane. This sunscreen agent is marketed under the trademark "Eusolex 8020" by Merck, and has the following structural formula:

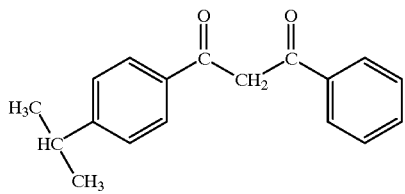

The subject dibenzoylmethane derivative(s) are advantageously present in the compositions stabilized in accordance with the present invention in contents generally ranging from 0.01% to 10% by weight, and preferably in contents ranging from 0.3% to 5% by weight, relative to the total weight of the composition.

A second compound in the compositions according to the invention comprises a silane or organosiloxane compound substituted by a benzylidenecamphor functional group. These compounds are known to this art and are described, as well as processes for the synthesis thereof, in EP-A-0,325,881, EP-A-0,335,777 and EP-A-0,712,855.

The silane or organosiloxane compound bearing a benzylidenecamphor substituent according to the present invention preferably has the structural formula (I) below:

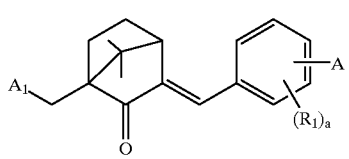

(I)

in which the radicals $R_1$, which may be identical or different, are each a hydrogen atom, an OH radical, a saturated or unsaturated, linear or branched, $C_1-C_{10}$ alkyl radical, a linear or branched $C_1-C_{10}$ alkoxy radical or an $—OSi(CH_3)_3$ radical, with the proviso that two adjacent groups $R_1$ may together form an alkylidenedioxy group in which the alkylidene radical contains 1 or 2 carbon atoms; a is an integer ranging from 1 to 3; A is a hydrogen atom or a radical of formula -L-W such that L is a divalent radical of formula (IIa) or (IIb) below:

$$—CH_2—CHR_2—[C(R_3)_2]_m—(CO)_n—(O)_o—(Z)_p—(Y)_q— \quad \text{(IIa)}$$

$$—CH=CR_2—[C(R_3)_2]_m—(CO)_n—(O)_o—(Z)_p—(Y)_q— \quad \text{(IIb)}$$

wherein $R_2$ and $R_3$, which may be identical or different, are each a hydrogen atom or a linear or branched $C_1-C_5$ alkyl radical, Z is a linear or branched, saturated or unsaturated $C_1$–$C_6$ diyl radical, optionally substituted with a hydroxyl or linear or branched, saturated or unsaturated $C_2$–$C_8$ alkyl radical, Y is —O—, —$NR_4$—, —$SO_2NH$—, —(CO)O—, —(CO)NH— or —O(CO)NH—, wherein $R_4$ is a hydrogen atom or a $C_1$–$C_5$ alkyl radical; m is an integer ranging from 0 to 10; n is 0 or 1; o is 0 or 1; p is 0 or 1; q is 0 or 1; $A_1$ is a hydrogen atom or a radical —$L_1$—W in which the radical $L_1$, has the definition of L, with the proviso that when q=1, then Y represents —$SO_2NH$—, with the further proviso that only one of the two radicals A and $A_1$, is a hydrogen atom; W is a radical of formula (1), (2) or (3) below:

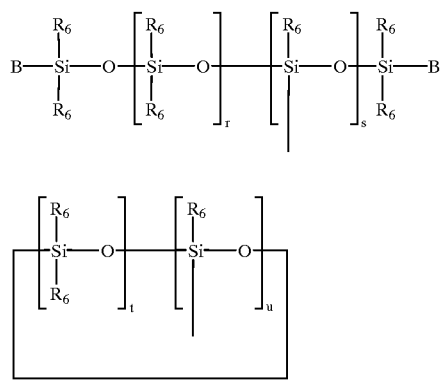

in which the radicals $R_6$, which may be identical or different, are each a linear or branched $C_1$–$C_{30}$ alkyl, phenyl, 3,3,3-trifluoropropyl or trimethylsilyloxy radical, at least 80%, by number, of the radicals $R_6$ being methyl radicals; the radicals B, which may be identical or different, are each a radical $R_6$ or a radical X of the formula below:

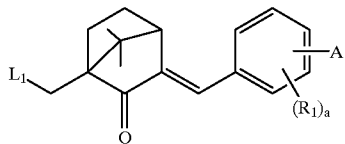

in which $R_1$, L, $L_1$ and a are as defined above; r is an integer ranging from 0 to 200, inclusive, and s is an integer ranging from 0 to 50, inclusive, and, if s=0, at least one of the two symbols B is X; u is an integer ranging from 1 to 10, inclusive, and t is an integer ranging from 0 to 10, inclusive, with the proviso that t+u is greater than or equal to 3.

Among the above compounds, particularly preferred is the family of compounds which has at least one, preferably all, of the following characteristics:

$R_1$=H, $OCH_3$, $CH_3$ or two adjacent radicals $R_1$ form a methylenedioxy radical, $R_2$=H or $CH_3$, n=0, a=1.

Among such compounds, preferred are those which have at least one, preferably all, of the following characteristics:

$R_6$ is methyl,

B is methyl, r ranges from 5 to 20, inclusive, s ranges from 2 to 15, inclusive, t+u ranges from 3 to 10, inclusive, m=1, and $R_3$ is a hydrogen atom or a methyl radical.

These compounds and the process for preparing same are described, for example, in EP-A-0,335,777.

A second family of preferred compounds comprises the compounds of formula (I) in which s=0.

Exemplary compounds of formula (I) which are particularly preferred are those of the following structural formulae:

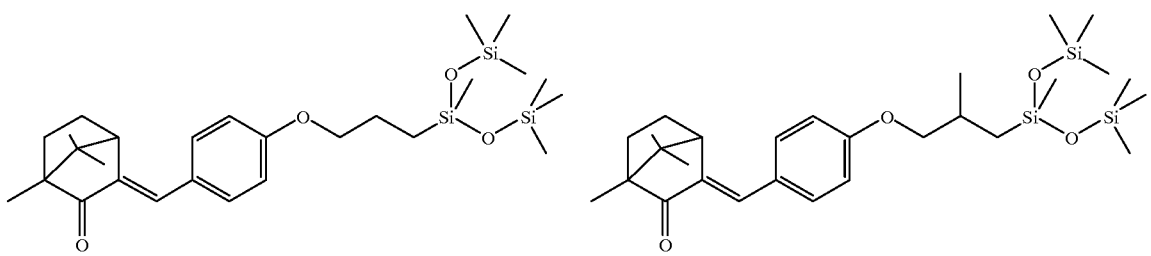

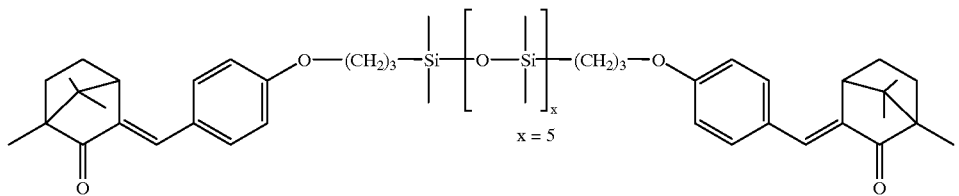

-continued

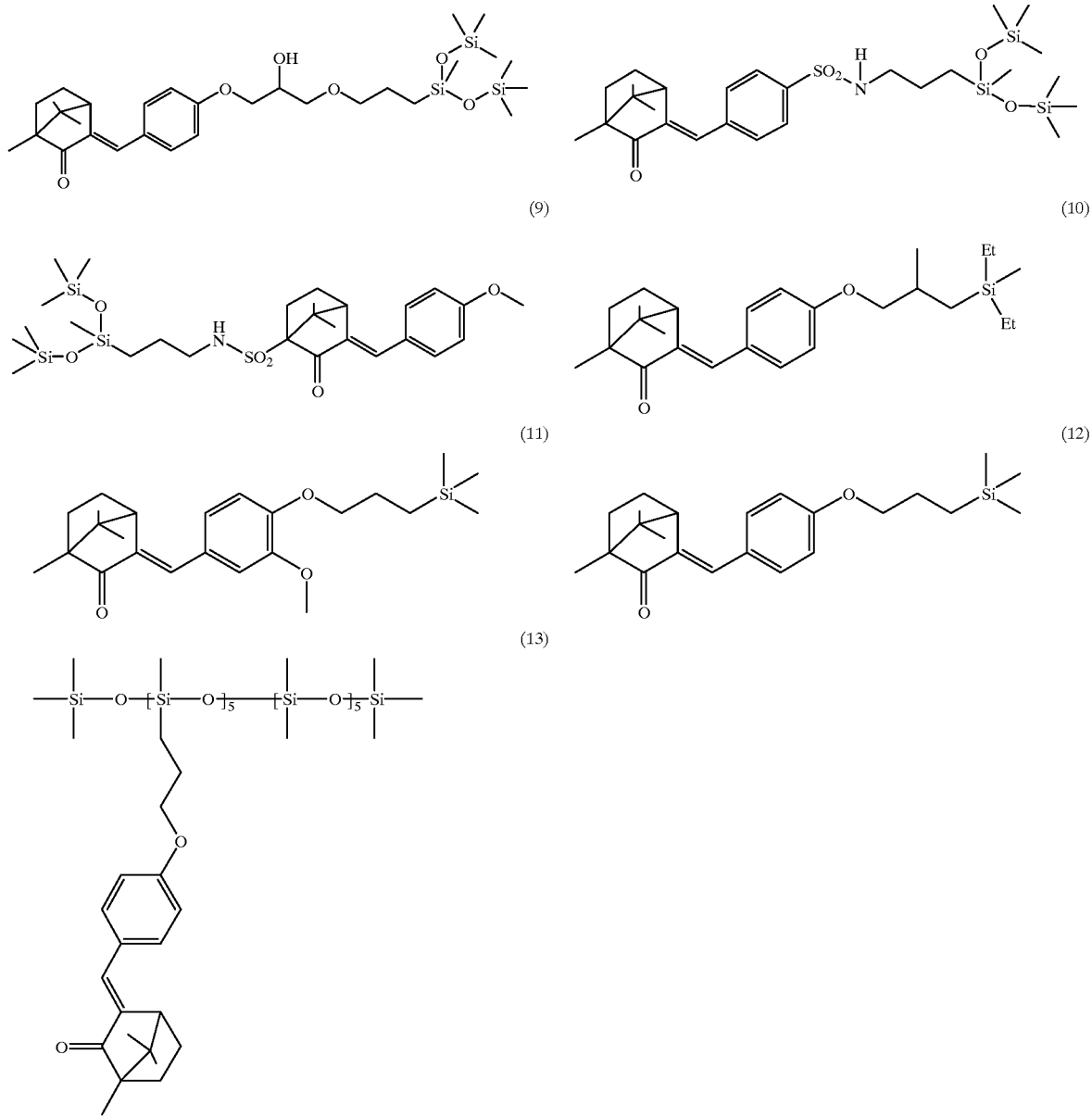

Among the compounds of formula (I), certain of these are novel and constitute another aspect of the present invention.

This is the case for the compounds of formula (I) as defined above in which p is 1 and the radical Z is a linear or branched, saturated or unsaturated $C_1$–$C_6$ diyl radical substituted by a hydroxyl or linear or branched, saturated or unsaturated $C_2$–$C_8$ alkyl radical. Exemplary of these specific compounds is the compound (7) as described above.

Another family of novel compounds of formula (I) includes the silane compounds in which W is a radical of formula (3) and n is equal to 0. Among such compounds, the compounds (10), (11) and (12) as described above are exemplary.

According to the invention, by the expression "effective amount of silane or organosiloxane compound bearing a benzylidenecamphor substituent" is intended an amount which is sufficient to provide an appreciable and significant improvement in the photostability of the dibenzoylmethane derivative(s) contained in the composition. The minimum amount of stabilizer to be formulated, which can vary depending on the nature of the cosmetically acceptable support (vehicle, diluent or carrier) selected for the composition, can be determined without any difficulty via a conventional test for measuring photostability, as described in FR-A-2,607,700.

The silane or organosiloxane compounds bearing a benzylidenecamphor substituent are generally present in the compositions according to the invention at a content at least equal to 0.5% by weight, relative to the total weight of the composition. Even more preferably, this content ranges from 0.5% to 20% by weight relative to the total weight of the composition.

Nonetheless, the cosmetic and/or dermatological compositions of the present invention can contain one or more complementary hydrophilic or lipophilic sunscreens that are active in the UV-A and/or UV-B range (absorbers). These complementary screening agents are advantageously selected from among cinnamic derivatives, salicylic derivatives, benzophenone derivatives, benzotriazole derivatives, benzimidazole derivatives, triazine derivatives, benzalmalonate derivatives, β,β'-diphenylacrylate derivatives, p-aminobenzoic acid derivatives, and the screening polymers and screening silicones described in WO-93/04665. Other examples of organic sunscreens are set forth in EP-A-0,487,404.

The compositions according to the invention can also contain agents for artificially tanning and/or browning the skin (self-tanning agents), such as, for example, dihydroxyacetone (DHA).

The cosmetic and/or dermatological compositions according to the invention can also contain pigments or nanopigments (average size of the primary particles: generally ranging from 5 nm to 100 nm, preferably from 10 to 50 nm) of coated or uncoated metal oxides, such as, for example, nanopigments of titanium dioxide (amorphous or crystallized in rutile and/or anatase form), of iron oxide, of zinc oxide, of zirconium oxide or of cerium oxide, which are all photoprotective agents that are well known per se, which act by physically blocking out (reflecting and/or scattering) the UV radiation. Conventional coating agents are, moreover, alumina and/or aluminum stearate. Such coated or uncoated metal oxide nanopigments are described, in particular, in EP-A-0,518,772 and EP-A-0,518,773.

The compositions of this invention can also comprise conventional cosmetic additives and adjuvants selected, in particular, from among fatty substances, organic solvents, ionic or nonionic thickeners, softeners, antioxidants, anti-free radical agents, opacifiers, stabilizers, emollients, silicones, hydroxy acids, antifoaming agents, moisturizers, vitamins, fragrances, preservatives, surfactants, fillers, sequestering agents, polymers, propellants, basifying or acidifying agents, colorants, dyes or any other ingredient usually used in the cosmetics and/or dermatological field, in particular for the manufacture of antisun compositions in the form of emulsions. Too, any additional ingredient liable to be introduced into the compositions in accordance with the invention must be such that it does not substantially affect or disrupt the photostabilizing effect exerted by the silane or organosiloxane compounds containing a benzylidenecamphor function with respect to the dibenzoylmethane derivatives.

Fatty substances can include an oil or a wax or mixtures thereof. By the term "oil" is intended a compound which is liquid at room temperature. By the term "wax" is intended a compound which is solid or substantially solid at room temperature and whose melting point is generally greater than 35° C.

Exemplary oils include the mineral oils (petroleum jelly); plant oils (sweet almond oil, macadamia oil, blackcurrant pip oil, jojoba oil); and synthetic oils such as perhydrosqualene, fatty alcohols, fatty acids or fatty esters (such as $C_{12}$–$C_{15}$ alkyl benzoate marketed under the trademark "Finsolv TN" by Finetex, octyl palmitate, isopropyl lanolate, triglycerides, including capric/caprylic acid triglycerides), oxyethylenated or oxypropylenated fatty esters and ethers; silicone oils (cyclomethicone, polydimethylsiloxanes or PDMS) or fluoro oils, and polyalkylenes.

Exemplary waxy compounds include paraffin, carnauba wax, beeswax and hydrogenated castor oil.

And exemplary organic solvents include the lower alcohols and polyols.

The thickeners are advantageously selected, in particular, from among crosslinked polyacrylic acids, and modified or unmodified guar gums and cellulose gums, such as hydroxypropyl guar gum, methylhydroxyethylcellulose and hydroxypropylmethyl cellulose.

The compositions according to the invention are easily formulated according to techniques which are well known to this art, in particular those intended for the preparation of emulsions of oil-in-water or water-in-oil type.

This compositions can be, in particular, in the form of a simple or complex (O/W, W/O, O/W/O or W/O/W) emulsion, such as a cream or a milk, or in the form of a gel or a cream-gel, a powder or a solid tube and can optionally be packaged as an aerosol and can be in the form of a mousse or a spray.

The compositions according to the invention are preferably formulated as oil-in-water emulsions.

When it is an emulsion, the aqueous phase thereof can comprise a nonionic vesicle dispersion prepared according to known techniques (Bangham, Standish and Watkins, *J. Mol. Biol.*, 13, 238 (1965), FR-2,315,991 and FR 2,416,008).

The cosmetic and/or dermatological compositions of the invention are useful for protecting the human epidermis or the hair against ultraviolet radiation, as an antisun composition or as a makeup product.

When the cosmetic compositions according to the invention are for protecting the human epidermis against UV rays, or as an antisun (sunscreen) composition, these can be formulated as suspensions or dispersions in solvents or fatty substances, in the form of a nonionic vesicle dispersion or in the form of an emulsion, preferably of oil-in-water type, such as a cream or a milk, in the form of an ointment, a gel, a cream-gel, a solid tube, a stick, a lotion, an aerosol mousse or a spray.

When the cosmetic compositions according to the invention are used for protecting the hair, same can be in the form of a shampoo, a lotion, a gel, an emulsion or a nonionic vesicle dispersion, and can constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a permanent-waving, straightening, dyeing or bleaching composition for the hair.

When the subject compositions are used as makeup product for the eyelashes, the eyebrows or the skin, such as an epidermal treatment cream, a foundation, a lipstick, an eyeshadow, a face powder, a mascara or an eyeliner, same can be in solid or pasty, anhydrous or aqueous form, such as oil-in-water or water-in-oil emulsions, nonionic vesicle dispersions or alternatively suspensions.

For illustrative purposes, for the antisun formulations in accordance with the invention which contain a support of oil-in-water emulsion type, the aqueous phase (in particular comprising the hydrophilic screening agents) generally constituting from 5% to 95% by weight, preferably from 70% to 90% by weight, relative to the total weight of the overall formulation, the oily phase (in particular comprising the lipophilic screening agents) generally constitutes from 5% to 50% by weight, preferably from 10% to 30% by weight, relative to the entire formulation, and the (co)emulsifier(s) generally represent(s) from 0.5% to 20% by weight, preferably from 2% to 10% by weight, relative to the entire formulation.

In order to further illustrate the present invention and the advantages thereof, the following specific examples are given, it being understood that same are intended only as illustrative and in nowise limitative.

EXAMPLE 1

Preparation of the compound of formula (4):

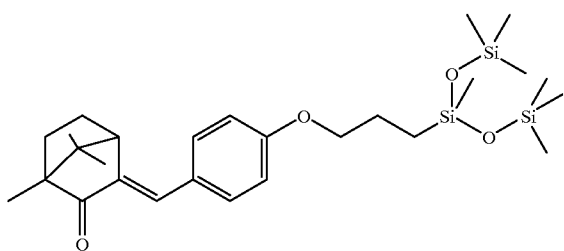

(4)

37.53 g (0.169 mol) of heptamethyltrisiloxane were added dropwise over 30 minutes to a solution of 3-(4-allyloxy-benzylidene)-1, 7,7-trimethylbicyclo[2.2.1]heptan-2-one, prepared in accordance with Example 8 of FR-A-2,430,938 (50 g, 0.169 mol), and of catalyst (complex containing 3%–3.5% by weight of Pt in cyclovinylmethylsiloxane marketed by Huls Petrarch PC085: 200 µl) in 140 ml of dry toluene heated to 80° C. The mixture was maintained at this temperature for 6 hours. The reaction mixture was concentrated. The residue was taken up in dichloromethane and this solution was passed through a bed of Celite. The pale yellow oil obtained was crystallized from heptane. 31 g (yield: 41%) of the target compound of this Example 1 were thus obtained in the form of a white powder:

m.p.: 47°–48° C. UV (95% ethanol) $\lambda_{max}$=318 nm, $\epsilon_{max}$= 27,000 Elemental analysis for $C_{27}H_{46}O_4Si_3$:

| Theory: | C62.50 | H8.94 | Si16.24 |
|---------|--------|-------|---------|
| Found:  | C62.43 | H9.00 | Si16.26 |

EXAMPLE 2

Preparation of the compound of formula (5):

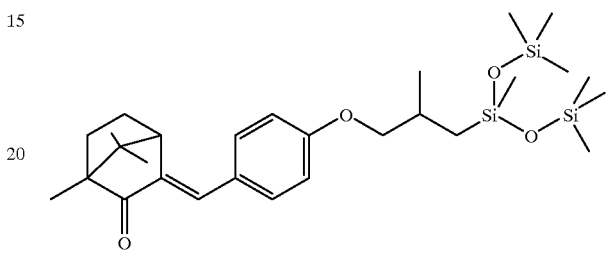

(5)

12.2 g (0.055 mol) of heptamethyltrisiloxane were added dropwise over 30 minutes to a solution of 1,7,7-trimethyl-3-[4-(2-methylallyloxy)benzylidene] bicyclo[2.2.1]heptan-2-one (15.5 g, 0.05 mol) and catalyst (complex containing 3%–3.5% by weight of Pt in cyclovinylmethylsiloxane marketed by Hüls Petrarch PC085:100 µl) in 35 ml of dry toluene heated to 80° C. The mixture was maintained at this temperature for 3 hours. The reaction mixture was concentrated and, after chromatography on silica (eluent: 50/50 heptane/dichloromethane), 23 g (yield: 86%) of a colorless oil of the target compound of this Example 2 were obtained:

UV (ethanol) $\lambda_{max}$=320 nm, $\epsilon_{max}$=26,200 Elemental analysis for $C_{28}H_{48}O_4Si_3$:

| Theory: | C63.10 | H9.08 | Si15.81 |
|---------|--------|-------|---------|
| Found:  | C63.02 | H9.00 | Si15.64 |

EXAMPLE 3

Preparation of the compound of formula (6):

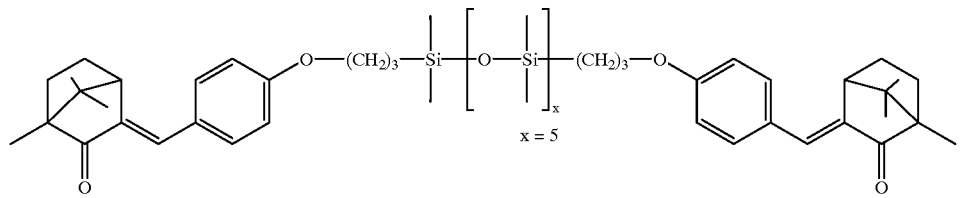

(6)

50 g (0.117 mol) of α,ω-dodecamethyl-hexasiloxane were added dropwise over 1 hour, 30 minutes, to a solution of 1,7,7-trimethyl-3-[4-(2-methylallyl- oxy)benzylidene] bicyclo[2.2.1]heptan-2-one (69.8 g, 0.235 mol) and of catalyst (complex containing 3%–3.5% by weight of Pt in cyclovinylmethylsiloxane marketed by Hüls Petrarch PC085: 100 μl) in 110 ml of dry toluene heated to 80° C. The mixture was maintained at this temperature for 1 hour, 30 minutes. The reaction mixture was concentrated and, after chromatography on silica (eluent: 98/2 heptane/ethyl acetate followed by gradient up to 50/50 heptane/ethyl acetate), 47.5 g (yield: 40%) of a viscous, pale yellow oil of the target compound of this Example 3 was obtained:

UV (ethanol) $\lambda_{max}$=320 nm, $\epsilon_{max}$=26,200 Elemental analysis for $C_{52}H_{86}O_9Si_6$:

| Theory: | C61.01 | H8.47 | Si16.46 |
| Found: | C61.04 | H8.52 | Si16.10 |

EXAMPLE 4

Preparation of the compound of formula (7):

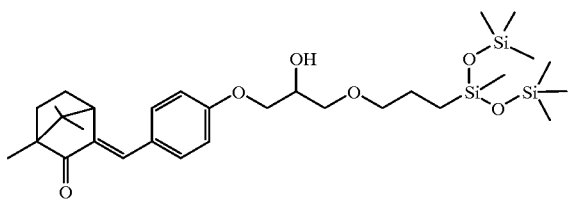

(7)

A mixture of 3-(4-hydroxybenzylidene)1,7, 7-trimethyl-N-bicyclo[2.2.1]heptan-2-one (10 g, 0.039 mol) and 3-glycidyloxypropyl-bis-(trimethylsiloxy) methylsilane (14.8 g, 0.044 mol) in the presence of tetrabutylammonium bromide (0.6 g) was maintained at 110° C. for 6 hours, while bubbling nitrogen there-through. The crude oil obtained was chromatographed on silica (eluent: 20/80 ethyl acetate/heptane) to give, in medium fractions, 10 g (yield: 43%) of the target compound of this Example 4 in the form of a colorless oil:

UV (ethanol) $\lambda_{max}$=318 nm, $\epsilon_{max}$=26,900 Elemental analysis for $C_{30}H_{52}O_6Si_3$:

| Theory: | C60.76 | H8.84 | Si14.21 |
| Found: | C60.54 | H8.87 | Si13.96 |

EXAMPLE 5

Preparation of the compound of formula (10):

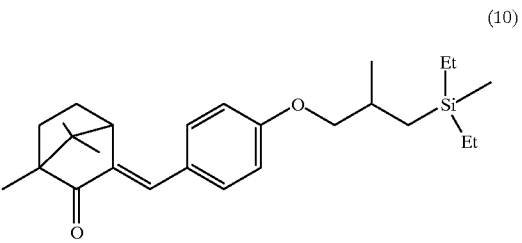

(10)

5.37 g (0.0525 mol) of diethylmethylsilane were added dropwise over 20 minutes to a solution of 1,7,7-trimethyl-3-[4-(2-methylallyloxy)benzylidene]bicyclo[2.2.1]heptan-2-one (15.5 g, 0.05 mol) and of catalyst (complex containing 3t–3.5% by weight of Pt in cyclovinylmethylsiloxane marketed by Hüls Petrarch PC085: 200 μl) in 10 ml of dry toluene heated to 70° C. The mixture was maintained at this temperature for 48 hours. The reaction mixture was concentrated and, after chromatography on silica (eluent: heptane/dichloromethane), 11.8 g (yield: 57%) of a viscous colorless oil of the target compound of this Example 5, which crystallized, were obtained:

m.p.: 39°–40° C.

UV (ethanol) $\lambda_{max}$=320 nm, $\epsilon_{max}$=28,230 Elemental analysis for $C_{26}H_{40}O_2Si$:

| Theory: | C75.67 | H9.77 | Si6.81 |
| Found: | C75.42 | H9.77 | Si7.10 |

EXAMPLE 6

Preparation of the compound of formula (11):

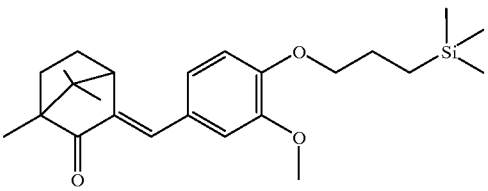

(11)

(a) First step: Preparation of 3-mnethozy-4-(3-trimethylsilanylproploxy) benzaldehyde:

3-chloropropyltrimethylsilane (33.14 g, 0.22 mol) was added dropwise over 20 minutes to a mixture of vanillin (30.4 g, 0.2 mol) and potassium carbonate (30.4 g, 0.22 mol) in 150 ml of dry DMF heated to 80° C. under nitrogen. The mixture was maintained for 4 hours at 95°–110° C. The reaction mixture was cooled and poured into ice-cold water. The aqueous phase was extracted three times with dichloromethane. The organic phases were dried over sodium sulfate and concentrated under vacuum. After distillation under vacuum (0.04 mm Hg), 47.5 g (yield: 89%) of 3-methoxy-4-(3-trimethylsilanylpropyloxy) benzaldehyde were obtained in the form of a slightly pinkish oil distilling at 112°–114° C. and employed without further purification in the following step.

(b) Second step: Preparation of the target compound of this Example 6:

A mixture of camphor (8.36 g, 0.055 mol) and NaH at 50% in oil (2.64 g, 0.055 mol; rinsed with dry heptane and then with dry dimethoxyethane) in 40 ml of dry dimethoxyethane was heated at 80° C. for 30 minutes. The step (a) derivative (13.32 g, 0.05 mol) dissolved in 30 ml of dimethoxyethane was added dropwise thereto over 20 minutes at 80° C. The mixture was maintained under stirring at 80° C. for 3 hours. After cooling, the mixture was poured into ice-cold water. The precipitate obtained was washed with water and then recrystallized from ethanol to give 12.4 g (yield: 62%) of the target compound of this Example 6 in the form of a white powder:

m.p.: 79°–80° C.

UV (ethanol) $\lambda_{max}$=331 nm, $\epsilon_{max}$=21,300 Elemental analysis for $C_{24}H_{36}O_3Si$:

| Theory: | C71.95 | H9.06 | Si7.01 |
| Found: | C71.80 | H9.05 | Si6.80 |

EXAMPLE 7

Preparation of the compound of formula (12):

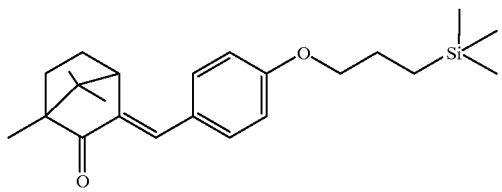

(12)

(a) First step: preparation of 4-(3-trimethylsilanylpropyloxy)benzaldehyde:

3-chloropropyltrimethylsilane (33.14 g, 0.22 mol) was added dropwise over 10 minutes to a mixture of 4-hydroxybenzaldehyde (24.4 g, 0.2 mol) and potassium carbonate (30.4 g, 0.22 mol) in 150 ml of dry DMF maintained at 120° C. under nitrogen. The mixture was maintained for 2 hours, 30 minutes, at 120°–130° C. The reaction mixture was cooled and poured into ice-cold water. The aqueous phase was extracted 3 times with dichloromethane. The organic phases were dried over sodium sulfate and concentrated under vacuum. After distillation under vacuum (0.2 mmHg), 40.5 g (yield: 86%) of 4-(3-trimethylsilanylpropyloxy) benzaldehyde were obtained in the form of a colorless oil distilling at 110–114° C. and employed without further purification in the following step.

(b) Second step: preparation of the target compound of this Example 7:

A mixture of camphor (15.2 g, 0.1 mol) and NaH at 50% in oil (4.8 g, 0.1 mol); rinsed with dry heptane and then with dry dimethoxyethane) in 50 ml of dry dimethoxyethane were heated at 80° C. for 30 minutes. The above step (a) derivative (21.3 g, 0.09 mol) dissolved in 30 ml of diethoxyethane was added dropwise thereto over 20 minutes at 80° C. The mixture was maintained under stirring at 80° C. for 2 hours.

After cooling, the mixture was poured into ice-cold water. The precipitate obtained was washed with water and then recrystallized from ethanol to give 20.6 g (yield: 60%) of the target compound of this Example 7 in the form of a white powder:

m.p.: 100°–101° C.

UV (ethanol) $\lambda_{max}$=320 nm, $\epsilon_{max}$=26,530 Elemental analysis for $C_{23}H_{34}O_2Si$:

| Theory: | C74.54 | H9.25 | Si7.58 |
| Found: | C74.62 | H9.17 | Si7.80 |

EXAMPLE 8

The compositions described below were formulated (the amounts are expressed as a % by weight relative to the total weight of the composition):

| Composition A (comparative): | |
| --- | --- |
| Ingredients | Composition A |
| Isopropyl myristate | 30 |
| Parsol 1789 | 1.5 |
| Ethanol | q.s. 100 |

| Composition A' (comparative): | |
| --- | --- |
| Ingredients | Composition A' |
| Isopropyl myristate | 30 |
| 3-(4-methylbenzylidene-camphor (Eusolex 6300) | 5 |
| Parsol 1789 | 1.5 |
| Ethanol | q.s. 100 |

The following compositions B to E (according to the present invention) also comprised 5% by weight of a silicone benzylidenecamphor compound of this invention.

| Ingredients | Composition B | Composition C | Composition D | Composition E |
| --- | --- | --- | --- | --- |
| Isopropyl myristate | 30 | 30 | 30 | 30 |
| Parsol 1789 | 1.5 | 1.5 | 1.5 | 1.5 |
| Silicone benzyl-idene-camphor according to the invention | Example 5 | Example 6 | Example 7 | Example 2 |
| Ethanol | qs 100 | qs 100 | qs 100 | qs 100 |

For each of these compositions, the percentage of residual Parsol 1789 (4-tert-butyl-4'-methoxydibenzoylmethane) after irradiation with UV according to the following procedure was determined: for each formula, three control samples and three test samples were prepared. 2 $\mu l/cm^2$ of formula were spread by hand onto frosted glass plates. The plates were then exposed in a chamber, the temperature of which was adjusted to about 35°–40° C. (Heraeus Suntest CPS) for the time required to obtain an exposure, expressed relative to the UVA flux, of 30 J/cm², in order to simulate natural UV irradiation by storing the control plates in darkness during the period of irradiation of the other plates.

The samples were then assayed in the following manner: the screening agents were extracted by immersing each plate in 50 g of ethanol in order to dissolve the screening agents. The plates and the solvent containing the screening agents were then treated with ultrasound for 15 minutes in order to ensure efficient extraction. The solutions obtained were analyzed by spectrophotometry at the $\lambda_{max}$ of each of the screening agents.

For each test formula, the level of residual 4-tert-butyl-4'-methoxydibenzoylmethane after irradiation was given by the ratio of its concentration in the irradiated sample to its concentrated in the non-irradiated sample.

The results, as a percentage of 4-tert-butyl-4'-methoxydibenzoylmethane remaining, are reported in the Table below:

TABLE

| Composition | OD % of residual Parsol 1789 |
|---|---|
| Composition A (comparative) | 5 ± 1 |
| Composition A' (comparative) | 58.8 |
| Composition B (invention) | 76 ± 6 |
| Composition C (invention) | 81 ± 6 |
| Composition D (invention) | 79 ± 7 |
| Composition E (invention) | 69 ± 3 |

These results clearly evidenced that the presence of a silane or organosiloxane compound containing a benzylidenecamphor group improved the photostability of 4-tert-butyl-4'-methoxydibenzoylmethane.

These results also evidenced that the photostability of 4-tert-butyl-4'-methoxydibenzoyl-methane obtained in the presence of a hydrocarbon-based benzylidenecamphor compound was further improved by formulating therewith, in place of the latter compound, silane or organosiloxane compounds containing a benzylidenecamphor group.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for photostabilizing a topically applicable cosmetic/dermatological sunscreen composition suited for the UV-photoprotection of human skin and/or hair comprising a photoprotecting effective amount of at least one dibenzoylmethane UV-screening compound, said method comprising admixing into said composition an amount of at least one silane or organosiloxane substituted by a benzylidenecamphor functional group effective to photostabilize said at least one dibenzoylmethane UV-screening compound.

2. The method as defined by claim 1, wherein said at least one silane or organosiloxane substituted by a benzylidenecamphor functional group has the structural formula (I):

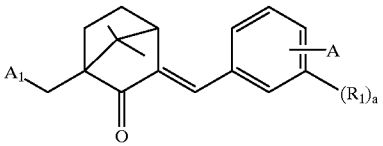

(I)

in which the radicals $R_1$, which may be identical or different, are each a hydrogen atom, an OH radical, a saturated or unsaturated, linear or branched, $C_1$–$C_{10}$ alkyl radical, a linear or branched $C_1CO_{10}$ alkoxy radical or an —OSi $(CH_3)_3$ radical, with the proviso that two adjacent groups $R_1$ may together form an alkylidenedioxy group in which the alkylidene radical contains 1 or 2 carbon atoms; a is an integer ranging from 1 to 3; A is a hydrogen atom or a radical of the formula —L—W wherein L is a divalent radical of formula (IIa) or (Iub) below:

(IIa)

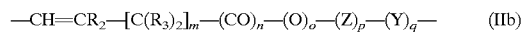

(IIb)

in which the radicals $R_2$ and $R_3$, which may be identical or different, are each a hydrogen atom or a linear or branched $C_1$–$C_5$ alkyl radical, Z is a linear or branched, saturated or unsaturated $C_1$–$C_6$ diyl radical, optionally substituted with a hydroxyl or linear or branched, saturated or unsaturated $C_2$–$C_8$ alkyl radical, Y is —O—, —$NR_4$—, —$SO_2NH$—, —(CO)O—, —(CO)NH— or —O(CO)NH—, wherein $R_4$ is a hydrogen atom or a $C_1$–$C_5$ alkyl radical; m is an integer ranging from 0 to 10; n is 0 or 1; o is 0 or 1; p is 0 or 1; q is 0 or 1; $A_1$ is a hydrogen atom or a radical —$L_1$—W in which the radical $L_1$ has the definition of L, with the proviso that, when q=1, then Y is —$SO_2NH$—, with the further proviso that only one of the two radicals A and $A_1$ is a hydrogen atom; W is a radical of formula (1), (2) or (3) below:

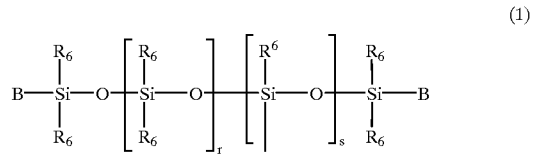

(1)

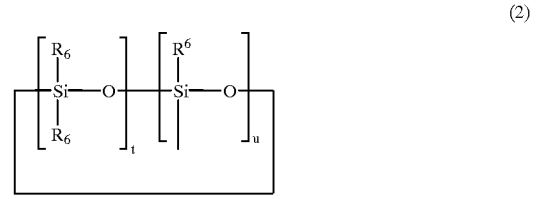

(2)

in which the radicals $R_6$, which may be identical or different, are each a linear or branched $C_1$–$C_{30}$ alkyl, phenyl, 3,3,3-trifluoropropyl or trimethylsilyloxy radical, at least 80%, by number, of the radicals $R_6$ being methyl radicals; the radicals B, which may be identical or different, are each a radical $R_6$ or a radical X of the formula below:

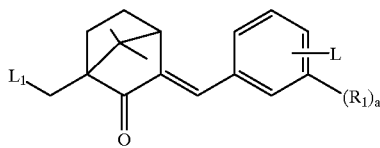

in which $R_1$, L, $L_1$ and a are as defined above; r is an integer ranging from 0 to 200, inclusive, and s is an integer ranging from 0 to 50, inclusive, and, if s=0, at least one of the two symbols B is X; u is an integer ranging from 1 to 10, inclusive, and t is an integer ranging from 0 to 10, inclusive, with the proviso that t+u is greater than or equal to 3.

3. The method as defined in claim 2, wherein in formula (I), at least one of the following conditions is satisfied:

$R_1$=H, $OCH_3$, $CH_3$ or two adjacent radicals $R_1$ together form a methylenedioxy group;

$R_2$=H or $CH_3$, n=0, q=1.

4. The method as defined by claim 2, wherein in formula (I), at least one of the following conditions is satisfied:

$R_6$ is methyl;

B is methyl;

r ranges from 5 to 20, inclusive;

s ranges from 2 to 15, inclusive;

t+u ranges from 3 to 10, inclusive;

m=1;

$R_3$ is a hydrogen atom or a methyl radical.

5. The method as defined by claim 2, wherein in formula (I), s=0.

6. The method as defined by claim 2, wherein said at least one compound having the formula (I) is selected from among those of the following structural formulae:

(4)

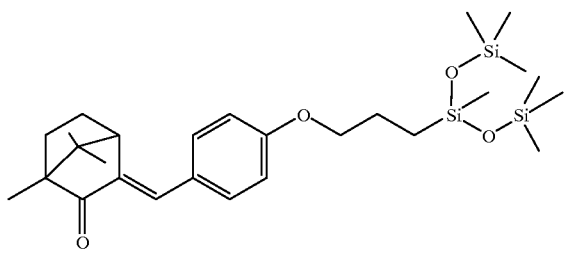

(5)

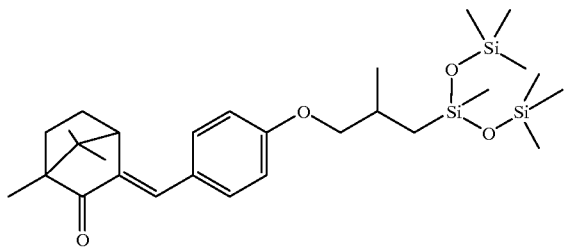

(6)

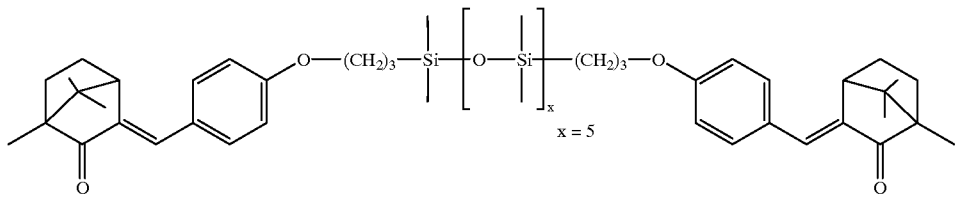

(7)

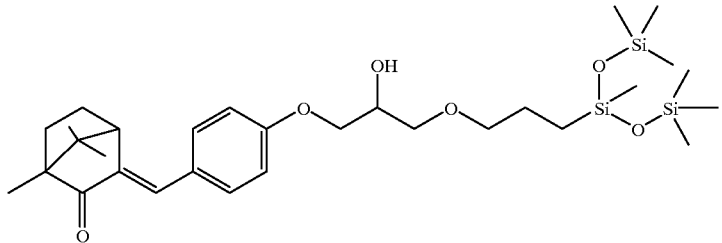

-continued
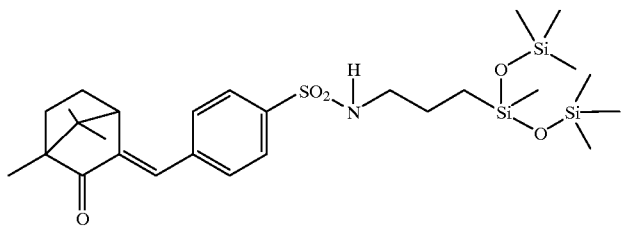
(8)
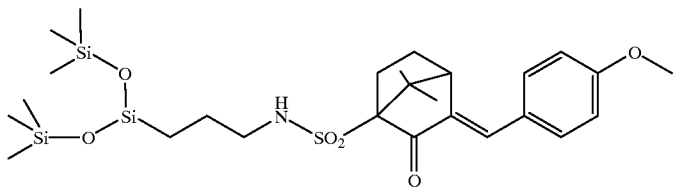
(9)
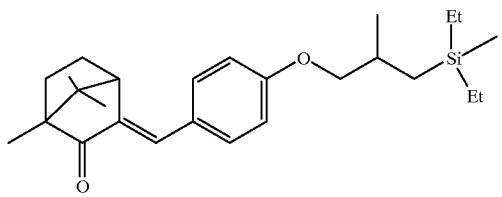
(10)
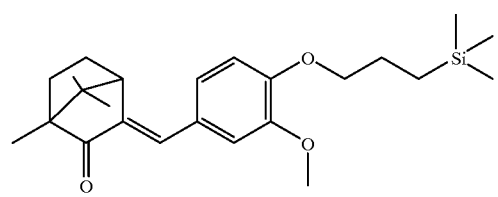
(11)
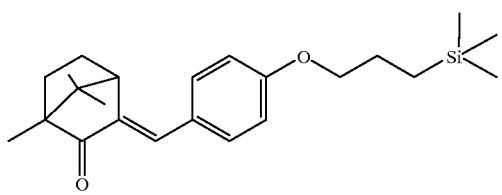
(12)
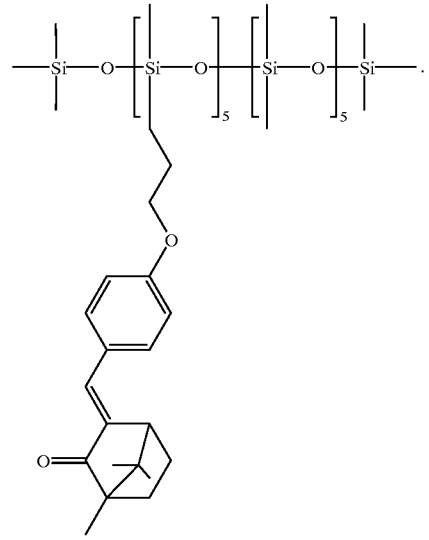
(13)
7. The method as defined by claim 2, wherein in formula (I), p is equal to 1 and the radical Z is a linear or branched, saturated or unsaturated $C_1$–$C_6$ diyl radical substituted by a hydroxyl or linear or branched, saturated or unsaturated $C_2$–$C_8$ alkyl radical.
8. The method as defined by claim 7, wherein said at least one formula (I) compound has the structural formula (7):
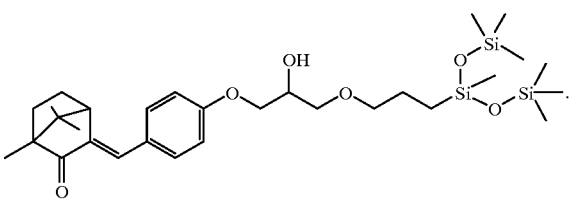
(7)

9. The method as defined by claim 2, wherein in formula (I), W is a radical of formula (3) and n=0.

10. The method as defined by claim 9, wherein said at least one compound having the formula (I) is selected from among those of the following structural formulae:

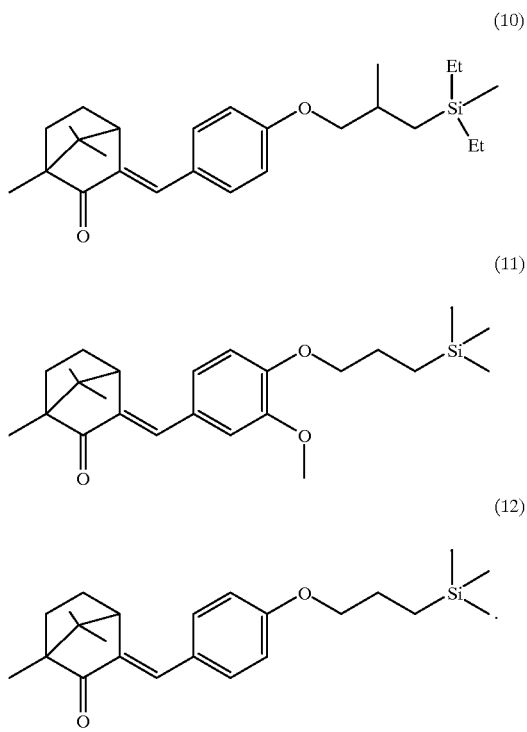

11. The method as defined by claim 2, wherein said at least one dibenzoylmethane UV-screening compound comprises
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane, and/or
2,6-dimethyl-4-tert-butyl-4'-methoxydibenzoylmethane.

12. The method as defined by claim 11, wherein said at least one dibenzoylmethane UV-screening compound comprises 4-(tert-butyl)-4'-methoxydibenzoylmethane.

13. The method as defined by claim 11, wherein said at least one dibenzoylmethane UV-screening compound comprises 4-isopropyldibenzoylmethane.

14. The method as defined by claim 1, wherein said composition is formulated into a topically applicable, cosmetically/dermatologically acceptable vehicle, diluent or carrier therefor.

15. The method as defined by claim 1, wherein said composition comprises from 0.01% to 10% by weight of said at least one dibenzoylmethane UV-screening compound.

16. The method as defined by claim 1, wherein said composition comprises from 0.01% to 6% by weight of said at least one dibenzoylmethane UV-screening compound.

17. The method as defined by claim 15, wherein said composition comprises at least 0.5% by weight of said at least one substituted silane or organosiloxane.

18. The method as defined by claim 15, wherein said composition comprises from 0.5% to 20% by weight of said at least one substituted silane or organosiloxane.

19. The method as defined by claim 1, wherein said composition comprises an oil-in-water emulsion.

20. The method as defined by claim 1, wherein said composition comprises a water-in-oil emulsion.

21. The method as defined by claim 1, wherein said composition further comprises at least one additional hydrophilic or lipophilic organic UV-A and/or UV-B sunscreen.

22. The method as defined by claim 21, wherein said composition further comprises at least one cinnamic derivative, salicylic derivative, triazine derivative, benzotriazole derivative, benzimidazole derivative, benzophenone derivative, β,β-diphenylacrylate derivative, p-aminobenzoic acid derivative, sunscreen polymer, or sunscreen silicone.

23. The method as defined by claim 1, wherein said composition further comprises a photoprotecting effective amount of particulates of at least one inorganic pigment or nanopigment.

24. The method as defined by claim 23, wherein said at least one pigment or nanopigment comprises titanium dioxide, zinc oxide, iron oxide, zirconium oxide, cerium oxide, or mixture thereof.

25. The method as defined by claim 1, wherein said composition further comprises at least one active agent for the artificial tanning and/or browning of human skin.

26. The method as defined by claim 1, wherein said composition further comprises at least one cosmetically acceptable adjuvant or additive.

27. The method as defined by claim 26, wherein said at least one adjuvant or additive comprises a fat, organic solvent, ionic or nonionic thickening agent, softener, antioxidant, anti-free-radical antioxidant, opacifying agent, stabilizing agent, emollient, silicone, hydroxy acid, antifoaming agent, hydrating agent, vitamin, fragrance, preservative, surfactant, filler, sequestering agent, polymer, propellant, basifying of acidifying agent, dye colorant, or mixture thereof.

28. The method as defined by claim 1, wherein said composition comprises a nonionic vesicle dispersion, emulsion, cream, milk, gel, cream gel, ointment, suspension, dispersion, powder, solid stick, foam or spray.

29. The method as defined by claim 1, wherein said composition comprises a makeup.

30. The method as defined by claim 29, wherein said composition comprises an anhydrous or aqueous solid or paste, emulsion, suspension, or dispersion.

31. The method as defined by claim 1, wherein said composition comprises a shampoo, lotion, gel, emulsion, non-ionic vesicle dispersion, hair lacquer, or rinse.

* * * * *